(12) United States Patent
Agostini et al.

(10) Patent No.: US 6,296,858 B1
(45) Date of Patent: Oct. 2, 2001

(54) COSMETIC COMPOSITION COMPRISING AN AQUEOUS DISPERSION OF FILM-FORMING POLYMER PARTICLES CONTAINING 1,2-PENTANEDIOL

(75) Inventors: Isabelle Agostini, Chatenay Malabry; Sylvle Cupferman, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/249,065

(22) Filed: Feb. 12, 1999

(51) Int. Cl.⁷ .............................. A61K 6/00; A61K 7/00; A61K 7/04; A61K 7/025; A01N 25/34
(52) U.S. Cl. .............................. 424/401; 424/61; 424/64; 424/70.7; 424/404
(58) Field of Search .................................. 424/70.7, 401, 424/404, 61, 64, 59; 514/937

(56) References Cited

U.S. PATENT DOCUMENTS

| | | | |
|---|---|---|---|
| 5,348,998 | * | 9/1994 | Ito et al. ............................... 524/190 |
| 5,624,906 | * | 4/1997 | Vermeer ................................. 514/23 |
| 6,113,888 | * | 9/2000 | Castro et al. .......................... 424/59 |

FOREIGN PATENT DOCUMENTS

| | | |
|---|---|---|
| 0 657 157 | 6/1995 | (EP) . |
| 0 479 850 | 5/1996 | (EP) . |
| 0 687 461 | 10/1996 | (EP) . |
| 0 775 483 | 5/1997 | (EP) . |
| 0 6 555 234 | 10/1998 | (EP) . |
| 0 745 372 | 11/1998 | (EP) . |
| 0 679 384 | 10/2000 | (EP) . |
| 1 594 624 | 7/1970 | (FR) . |
| 48-14931 | 5/1973 | (JP) . |
| 7-187956 | 7/1995 | (JP) . |
| 7-196462 | 8/1995 | (JP) . |
| H 8-22534 | 9/1996 | (JP) . |
| H 8-225433 | 9/1996 | (JP) . |
| 8-333222 | 12/1996 | (JP) . |
| 100-53510 | 2/1998 | (JP) . |
| 10-158129 | 6/1998 | (JP) . |
| WO 93/20812 | 10/1993 | (WO) . |
| WO 95/01151 | 1/1995 | (WO) . |
| WO 96/11572 | 4/1996 | (WO) . |
| WO 97/30692 | 8/1997 | (WO) . |
| WO 97/47310 | 12/1997 | (WO) . |
| WO 98/03152 | 1/1998 | (WO) . |

OTHER PUBLICATIONS

Proserpio et al., "Sostanze "Non Conservanti" in Grado di Inibire la Crescita Microbica nei Cosmetici", Cosmetics & Toiletries, Ed. It. N 3/96, 11–13, 16–19, 1996 (English language Abstract also attached).

Oana–Arina Antoce, et al., "Calorimetric Evaluationof the Antimicrobial Properties of 1,3–butanediol and 1,2–pentanediol on Various Microorganisms", Netsu Sokutel vol. 25, No. 1, pp. 2–8 (1998).

* cited by examiner

Primary Examiner—Thurman K. Page
Assistant Examiner—S. Howard
(74) Attorney, Agent, or Firm—Nixon & Vanderhye P.C.

(57) ABSTRACT

The invention relates to the use in a cosmetic or dermatological composition which can be applied to the skin, keratin fibres, semi-mucous membranes and/or mucous membranes, of an aqueous dispersion of film-forming polymer particles combined with an antimicrobial protection system, in particular an antibacterial and/or antifungal system, comprising 1,2-pentanediol. The invention relates in particular to a make-up composition for the lips or the body.

49 Claims, No Drawings

COSMETIC COMPOSITION COMPRISING AN AQUEOUS DISPERSION OF FILM-FORMING POLYMER PARTICLES CONTAINING 1,2-PENTANEDIOL

The present invention relates to a cosmetic or dermatological composition which can be applied to the skin, semi-mucous membranes, mucous membranes and/or keratin fibres. This composition comprises in particular an aqueous dispersion of film-forming polymer particles and of 1,2-pentanediol, and can be used as a care product and a make-up product.

It is advantageous to use an aqueous dispersion of film-forming polymer particles in cosmetic or dermatological compositions, as shown, for example, by Japanese patent applications H8-225,433 and H8-225,434 and patent applications EP-A-8,679,384, EP-A-0,687,461 and EP-A-0,775,483.

Such compositions contain large proportions of aqueous phase, generally more than 50%. These aqueous compositions are fully tolerated by the body. On the other hand, the large portion occupied therein by water makes them favoured targets for the intrusion of moulds, bacteria and other microorganisms. This microbial contamination can arise during manufacture of the product and especially during its use by the consumer, and is particularly appreciable in the case of lipsticks and aqueous nail varnishes which require the use of an applicator brush which is continually immersed in a bottle which, on account of the frequent removals from and replacements in the bottle containing the product, promotes recontamination of the product at each use.

It thus proved to be necessary to develop antimicrobial protection for cosmetic and dermatological compositions containing an aqueous dispersion of film-forming polymer particles.

The development of an antimicrobial protection system for this type of composition has been complicated by many constraints regarding the choice of antimicrobial agents, and in particular;
  legal constraints, since the antimicrobial agents selected need to be authorized for an application on mucous membranes and semi-mucous membranes;
  solubility constraints: in the absence of a fatty phase in the formulation, the antimicrobial protection system must be totally water-soluble;
  implementation temperature constrains: the water-solubility of the antimicrobial agent must be complete under cold conditions, since the formulation does not tolerate heating: when an aqueous dispersion of polymer particles is heated, the particles flocculate at a temperature above 45° C.;
  pH constraints; the antimicrobial protection system must be effective at the pH of the formulation, and in particular at pH values of from 6 to 8.5, the pH of a composition applied to the skin generally being neutral, and this being in the absence of an acidic-pH regulator; the reason for this is that it is known that most bacteria and fungi are not resistant at acidic pH;
  constraints of compatibility with the aqueous dispersion of polymer particles, which exhibits many incompatibilities; for example, chlorhexidine, which is generally used as a preserving agent in cosmetics and dermatology, cannot be used in the presence of an aqueous dispersion of polymer particles.

After having carried out many tests in order to arrive at an antimicrobial protection system, in particular an antibacterial and/or antifungal system, which satisfies all the above criteria, the Applicant has discovered that 1,2-pentanediol is entirely suitable for use as an antimicrobial agent in an aqueous dispersion of film-forming polymer particles.

1,2-Pentanediol, also known as pentylene glycol (CTFA name) is known in cosmetics as a bactericidal and fungicidal agent (G. Proserpio and R. Cattaneo, Cosmetics and Toiletries, It. Ed., No. 3/1996, 11–13, 16–19) and as a skin moisturization regulator (patent application WO-A-95/01151). It is also described for the topical treatment of the skin and the scalp, on account of its antimicrobial effect, in patent application WO-A-97/30692.

However, it has never been used in the presence of an aqueous dispersion of polymer particles.

The Applicant has discovered that, on account of its antibacterial and antifungal properties, 1,2-pentanediol not only makes it possible to protect the aqueous dispersion of polymer particles, but also has properties of plasticizing the polymer in dispersion, which makes it possible to limit the use of standard plasticizers such as other glycols (glycerol, propylene glycol) and thus to reduce the sticky feel of the composition. It also has moisturizing properties, which is important for the skin and the lips, as well as antifreeze properties and in addition has the advantage of making the composition shinier than when a standard preserving agent is used, and achieves this without adversely affecting the long-lasting and/or "transfer-resistant" properties of this composition, which is entirely surprising and highly desired for nail varnishes and lipsticks.

Thus, one subject of the invention is the use, in a cosmetic or dermatological composition which can be applied to the skin, keratin fibres, semi-mucous membranes and/or mucous membranes, of an aqueous dispersion of film-forming polymer particles combined with an antimicrobial protection system, in particular an antibacterial and/or antifungal system, comprising 1,2-pentanediol.

Another subject of the invention is the use, for making up, protecting and/or non-therapeutically treating and/or for the manufacture of a composition intended to therapeutically treat the skin, keratin fibres, semi-mucous membranes and/or mucous membranes, in particular. The facial lips and the body, of an aqueous dispersion of film-forming polymer particles combined with an antimicrobial protection system, in particular an antibacterial and/or antifungal system, comprising 1,2-pentanediol.

Another subject of the invention is a cosmetic or dermatological composition which can be applied to the skin, keratin fibres, semi-mucous membranes and/or mucous membranes, comprising an aqueous dispersion of film-forming polymer particles combined with an antimicrobial protection system, in particular an antibacterial and/or antifungal system, comprising 1,2-pentanediol.

Another subject of the invention is a make-up composition for the lips or the body comprising an aqueous dispersion of film-forming polymer particles combined with a antimicrobial protection system, in particular an antibacterial and/or antifungal system, comprising 1,2-pentanediol.

Another subject of the invention is a process for the antimicrobial protection of a composition containing an aqueous dispersion of film-forming polymer particles, which consists in introducing into the composition an antimicrobial protection system, in particular an antibacterial and/or antifungal system, comprising 1,2-pentanediol.

It has been found that the composition according to the invention is easy to apply and spreads easily and uniformly on the skin, semi-mucous membranes and mucous membranes, in particular on the facial lips and the body.

The composition according to the invention finds a particularly advantageous application in the field of caring for and/or making up facial skin and body skin, keratin fibres, mucous membranes and/or semi-mucous membranes. The term mucous membrane is intended in particular to refer to the inner part of the lower eyelid; the term semi-mucous membrane is intended more particularly to refer to the facial lips; the term keratin fibres is intended to refer in particular to the eyelashes, the eyebrows, the hair and the nails.

The composition according to the invention makes it possible to obtain a homogeneous film, which has a light texture and remains comfortable to wear throughout the day. The film is not at all sticky after drying. It is transfer-resistant and/or long-lasting.

The composition according to the invention thus finds a most particular application as a composition to be applied to the lips and the body, in particular as a lipstick and a semi-permanent body make-up product.

Moreover, the film obtained can be very shiny, or more or less matt, depending on the nature of the constituents in the composition, resulting in a wider range of make-up products which are shiny or matt, according to choice.

The composition according to the invention comprises at least one aqueous dispersion of film-forming polymer particles. It can be in the form of an aqueous or aqueous-alcoholic fluid, a paste or an emulsion. In the latter case, it can contain fatty substances such as oils and waxes.

Among the film-forming polymers which can be used in the present invention, mention may be made of synthetic polymers, such a polycondensates or radical polymers, polymers of natural origin, and mixtures thereof.

Mention may thus be made, among polycondensates, of anionic, cationic, nonionic or amphoteric polyurethanes, acrylic polyurethanes, polyurethane-polyvinylpyrrolidones, polyester-polyurethanes, polyether-polyurethanes, polyureas, polyurea-polyurethanes and mixtures thereof. The polyurethane can be, for example, an aliphatic, cycloaliphatic or aromatic polyurethane, polyurea/urethane or polyurea copolymer containing, alone or as a mixture:

- at least one sequence of linear or branched aliphatic and/or cycloaliphatic and/or aromatic poly-ester origin, and/or
- at least one sequence of aliphatic and/or cycloaliphatic and/or aromatic polyether origin, and/or
- at least one substituted or unsubstituted, branched or unbranched silicone sequence, for example polydimethylsiloxane or polymethylphenylsiloxane, and/or
- at least one sequence containing fluoro groups.

The polyurethanes as defined in the invention can also be obtained from branched or unbranched polyesters, or from alkyds containing labile hydrogens which are modified by reaction with a diisocyanate and a difunctional (for example dihydro, diamino or hydroxyamino) organic compound, in addition containing either a carboxylic acid- or carboxylate group, or a sulphonic acid or sulphonate group, or alternatively a neutralizable tertiary amine group or a quaternary ammonium group.

Mention may also be made of polyesters, polyesteramides, fatty-chain polyester, polyamides and epoxyester resins.

The polyesters can be obtained, in a known manner, by polycondensation of aliphatic or aromatic diacids with aliphatic or aromatic diols or polyols. Aliphatic diacids which can be used are succinic acid, glutaric acid, adipic acid, pimelic acid, suberic acid or sebacic acid. Aromatic diacids which can be used are terephthalic acid or isophthalic acid, or alternatively a derivative such as phthalic anhydride. Aliphatic diols which can be used are ethylene glycol, propylene glycol, diethylene glycol, neopentyl glycol, cyclo- hexanedimethanol and 4,4'-(1-methylpropylidene)-bisphenol. Polyols which can be used are glycerol pentaerythritol, sorbitol and trimethylolpropane.

The polyesteramides can be obtained in a similar manner to that for the polyesters, by polycondensation of diacids with diamines or amino alcohols. Diamines which can be used are ethylenediamine, hexamethylenediamine and meta- or para-phenylenediamine. An amino alcohol which can be used is monoethanolamine.

As a monomer bearing an anionic group which can be used in the polycondensation, mention may be made, for example, of dimethylolpropionic acid, trimellitic acid or a derivative such as trimellitic anhydride, the sodium salt of pentanediol-3-sulphonic acid or the sodium salt of 1,3-benzenedicarboxylic-5-sulphonic acid.

The fatty-chain polyesters can be obtained using fatty-chain diols in the polycondensation.

The epoxyester resins can be obtained by polycondensation of fatty acids with a condensate containing $\alpha\omega$-diepoxy ends.

The radical polymers can be, in particular, acrylic and/or vinyl polymers or copolymers. These polymers can result from the polymerization of ethylenically unsaturated monomers containing at least one acid group and/or esters of these acidic monomers and/or amides of these acidic monomers. Anionic radical polymers, i.e. polymers prepared from at least one monomer containing an acid group, are preferably used.

As a monomer bearing an acid group which can be used in the radical polymerization, mention may be made of $\alpha\beta$-ethylenic unsaturated carboxylic acids such as acrylic acid, methacrylic acid, crotonic acid, maleic acid, itaconic acid and 2-acrylamido-2-methylpropane-sulphonic acid. (Meth) acrylic acid is preferably used.

The acrylic polymers can result from the copolymerization of monomers chosen from acrylic acid or methacrylic acid and the esters and/or amides of acrylic acid or of methacrylic acid. Examples of ester-type monomers which may be mentioned more particularly are alkyl, in particular $C_1$–$C_{20}$ alkyl and preferably $C_1$–$C_8$ alkyl, methacrylates such as methyl methacrylate, ethyl methacrylate, butyl methacrylate, isobutyl methacrylate, 2-ethylhexyl methacrylate and lauryl methacrylate. Examples of amide-type monomers which can be mentioned are N-tert-butyl acrylamide and N-tert-octylacrylamide.

Acrylic polymers can be used which are obtained by copolymerization of ethylenically unsaturated monomers containing hydrophilic groups, preferably of nonionic nature, such as hydroxyethyl acrylate, 2-hydroxypropyl acrylate, hydroxyethyl methacrylate or 2-hydroxypropyl methacrylate.

The vinyl polymers can result from the homopolymerization or copolymerization of monomers chosen from vinyl esters, styrene, $\alpha$-methylstyrene and butadiene. Examples of vinyl esters which can be mentioned are vinyl acetate, vinyl neodecanoate, vinyl pivalate, vinyl benzoate and vinyl tert-butyl benzoate. In particular, these monomers can be polymerized with acidic monomers and/or their esters and/or their amides, such as those mentioned above.

Acrylic/silicone copolymers or nitrocellulose/acrylic copolymers can also be used.

The list of monomers given is not limiting and it is possible to use any monomer known to those skilled in the art in the categories of acrylic and vinyl monomers.

According to the invention, the film-forming polymer preferably used is chosen from (meth)acrylic acid/(meth)acrylate, (meth)acrylic acid/α-methyl-styrene, (meth)acrylate/styrene, (meth)acrylic acid/styrene, (meth)acrylate/(meth)acrylate and (meth)-acrylate/α-methylstyrene copolymers. Preferably, a copolymer derived from the copolymerization of $C_1$–$C_8$ alkyl methacrylate monomers, optionally combined with acrylic acid, with styrene and with α-methylstyrene is used.

The polymers of natural origin, which are optionally modified, can be chosen from shellac resin, sandarac gum, dammar resins, elemi gums, copal resins, cellulose derivatives and mixtures thereof.

Mention may also be made of the polymers resulting from the radical polymerization of one or more radical monomers inside and/or partially at the surface of pre-existing particles of at least one polymer chosen from the group consisting of polyurethanes, polyureas, polyesters, polyesteramides and/or alkyds. These polymers are generally known as hybrid polymers.

The aqueous dispersion comprising one or more film-forming polymers can be prepared by a person skilled in the art on the basis of his or her general knowledge.

The solids content of the aqueous dispersions according to the present invention can be about 5–70% by weight, and preferably 30–60% by weight, relative to the total weight of the dispersion.

The composition can comprise 1–60% by weight, preferably 5–40% by weight, of film-forming polymer solids.

The size of the polymer particles in aqueous dispersion can be between 5 and 500 nm and is preferably between 20 and 150 nm, which makes it possible to obtain a film with remarkable gloss.

The antimicrobial protection system according to the invention comprises:

in particular from 0.1 to 10% by weight, preferably 1 to 7% and optimally from 3 to 5% by weight, of 1,2-pentanediol;

0 to 5% by weight, advantageously 0.05 to 2% and preferably 0.2 to 1% by weight, of sodium methyl p-hydroxybezoate; and 0 to 40% by weight, advantageously 0.5 to 30% and preferably 1 to 10% by weight, of ethyl alcohol.

The composition can also comprise at least one water-soluble dye and/or at least one pigment, and/or at least one filler and/or at least one pearlescent agent, which are conventionally used in the cosmetics and make-up field.

The term pigments should be understood to mean white or coloured, inorganic or organic particles which are insoluble in the medium, intended to colour and/or opacify the composition, or to screen out UV rays. The pigments can be present in the composition in a proportion of 0–35% by weight of the final composition and preferably in a proportion of 1–20%. They can be white or coloured, inorganic and/or organic, of usual or nanometric size. Among the inorganic pigments and/or nanopigments which may be mentioned are titanium dioxide, zirconium dioxide or cerium dioxide, as well as zinc oxide, iron oxide or chromium oxide, and ferric blue. Among the organic pigments which may be mentioned are carbon black, barium, strontium, calcium (DC red No. 7) or aluminium lakes and cochineal carmine.

Among the water-soluble dyes which may be mentioned are the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll, and mixtures thereof.

The term fillers should be understood to mean colourless or white, inorganic or synthetic, lamellar or non-lamellar particles. The term pearlescent agents should be understood to mean iridescent particles, produced in particular by certain molluscs in their shells, or alternatively, synthesized. These fillers and pearlescent agents serve in particular to modify the texture of the composition.

The pearlescent agents can be present in the composition in a proportion of from 0 to 20% of the total weight of the composition, preferably at a high content from about 1 to 15%. Among the pearlescent agents which can be used in the invention, mention may be made of mica coated with titanium oxide, with iron oxide, with natural pigment or with bismuth oxychloride, such as coloured titanium mica.

The fillers can be present in a proportion of from 0 to 35% of the total weight of the composition, preferably 0.5 to 15%. Mention may be made in particular of talc, mica, kaolin, Nylon powders (in particular Orgasol) and polyethylene powders, Teflon, starch, boron nitride, copolymer microspheres such as Expancel (Nobel Industrie), Polytrap (Dow Corning) and silicone resin microbeads (for example Tospearl from Toshiba).

It is also possible to add to the composition according to the invention any known additive, such as thickeners, for example clays, gums, silicas, cellulose derivatives, a synthetic polymer such as an acrylic polymer or an associative polymer such as polyurethane, a natural gum such as xanthan gum, spreading agents, dispersing agents, antifoaming agents, UV screening agents, fragrances, cosmetic, pharmaceutical or dermatological active agents, vitamins and their derivatives, biological materials and their derivatives, surfactants for dispersing the pigments, waxes or oils.

Needless to say, a person skilled in the art will take care to select this or these optional additives and/or the amount thereof, such that the advantageous properties of the composition according to the invention are not, or are not substantially, adversely affected by the addition envisaged.

The pH of the final composition obtained is preferably less than 9.5, advantageously between 5 and 8.5 and preferably between 6 and 8.

Needless to say, this composition must be capable of being deposited on a support such as the skin, semi-mucous membranes or mucous membranes and keratin fibres.

The composition according to the invention can be in fluid, gelled, semi-solid, supple paste or even solid form, such as stick or tube.

It finds a application in particular as a make-up product, in particular as a lipstick, foundation, blusher, eyeshadow, eyeliner, mascara or nail varnish, or alternatively a make-up produce for the body such as a temporary or semi-permanent tattoo. An application in the field of care compositions, antisun compositions or self-tanning compositions, dermatological compositions or pharmaceutical compositions to be applied to the skin, semi-mucous membranes and/or mucous membranes may also be envisaged.

The invention is illustrated in greater detail in the examples below.

EXAMPLE 1

A fluid lipstick having the composition below is prepared:

| | |
|---|---|
| brown iron oxide | 4 g |
| sodium methyl p-hydroxybenzoate | 0.4 g |
| mixture of polyethylene wax and polytetrafluoroethylene in emulsion in a water/isopropanol mixture (50/47/3) | 4.5 g |
| methacrylic acid/poly(methoxyethylene glycol methacrylate)/lauryl methacrylate copolymer as a 40% solution in water/PPG (50/50) (dispersing agent) | 0.06 g |
| acrylic copolymer as an aqueous emulsion containing 45% solids, sold under the name "Neocryl A-1090" by the company Zeneca | 50 g |
| acrylic acid/ethyl acrylate copolymer as an unstabilized aqueous 28% emulsion (acrylic gelling agent) | 5.35 g |
| 60% solution of oxyethylenated oxypropylenated polydimethylsiloxane in dipropylene glycol monomethyl ether (antifoaming agent) | 0.1 g |
| non-denatured 96° ethyl alcohol | 5 g |
| 1,2-pentanediol | 3 g |
| sterilized demineralized water    q.s. | 100 g | a) The pigments are first ground in a mixture containing 1,2-pentanediol and water.

b) The Teflon-containing wax is mixed into the polymer dispersion at room temperature.

c) Some of the water, of the alcohol and of the sodium methyl p-hydroxybenzoate are mixed together and then added to the polymer dispersion obtained in b).

The antifoaming agent and then the mixture a) are added to this mixture obtained in c), at room temperature, along with the dispersing agent.

The mixture is completed with the remaining water, alcohol and sodium methyl p-hydroxybenzoate to obtain 100 g of composition.

The tests of antimicrobial efficacy carried out on this formulation by the artificial contamination test or "Challenge-test" on 6 microorganisms at 2 days, 7 days and 14 days, at room temperature, showed that the antimicrobial protection imparted by the system: sodium methyl p-hydroxybenzoate (0.4%), ethyl alcohol (5%) and 1,2-pentanediol (3%) was satisfactory since all of the 6 microorganisms inoculated *Escherichia coli, Pseudomonas aeruginosa, Staphylococcus aureus, Enterococcus faecalis, Candida albicans* and *Aspergillus niger*, are decontaminated 7 days after the inoculation.

The results are as follows.

| MICROORGANISMS | Inoculum microorganisms/gram | Ageing at room temperature | | |
|---|---|---|---|---|
| | | 2 J | 7 J | 14 J |
| *ESCHERICHIA COLI* | 5.6 × 10$^6$ | <2.0 × 10$^2$ | <2.0 × 10 | <2.0 × 10$^2$ |
| *PSEUDOMONAS AERUGINOSA* | 3.8 × 10$^6$ | <2.0 × 10 | <2.0 × 10$^2$ | <2.0 × 10$^2$ |
| *STAPHYLOCOCCUS AUREUS* | 1.6 × 10$^6$ | <2.0 × 10$^2$ | <2.0 × 10$^2$ | <2.0 × 10$^2$ |
| *ENTEROCOCCUS FAECALIS* | 2.8 × 10$^6$ | 6.0 × 10$^4$ | <2.0 × 10$^2$ | <2.0 × 10$^2$ |
| *CANDIDA ALBICANS* | 2.4 × 10$^6$ | <2.0 × 10$^2$ | <2.0 × 10$^2$ | <2.0 × 10$^2$ |
| *ASPERGILLUS NIGER* | 1.6 × 10$^6$ | 2.6 × 10$^4$ | <2.0 × 10$^2$ | <2.0 × 10$^2$ |

EXAMPLES 2 to 4

Formulations with the same composition as that of Example 1 were also tested, the amounts of the constituents in the antimicrobial protection system being varied as indicated below.

| Formulation | Sodium methyl p-hydroxybenzoate | 1,2-Pentanediol | Ethyl alcohol | Antimicrobial protection |
|---|---|---|---|---|
| Ex. 2 | 0.4% | 5% | — | acceptable |
| Ex. 3 | 0.4% | 5% | 5% | satisfactory |
| Ex. 4 | 0.4% | 5% | 3% | satisfactory |

The antimicrobial protection was evaluated in the same way as in Example 1, on the same microorganisms.

The antimicrobial protection is acceptable if not more than 2 of the 6 microorganisms tested are decontaminated only after 14 days. It is satisfactory if all 6 of the microorganisms inoculated are decontaminated 7 days after the inoculation.

The results are indicated below. They show that the antimicrobial protection systems in the formulations of Examples 2 to 4 according to the invention give these formulations, surprisingly, effective antimicrobial protection despite the small amount of preserving agent used, i.e. of 0.4% of sodium methyl p-hydroxybenzoate.

EXAMPLE 2

| Microorganisms | Inoculum micro-organisms/gram | Ageing at room temperature | | |
|---|---|---|---|---|
| | | 2 J | 7 J | 14 J |
| ESCHERICHIA COLI | $3.3 \times 10^6$ | $<2.0 \times 10^2$ | $<2.0 \times 10^2$ | $<2.0 \times 10^2$ |
| PSEUDOMONAS AERUGINOSA | $2.8 \times 10^6$ | $<2.0 \times 10^2$ | $<2.0 \times 10^2$ | $<2.0 \times 10^2$ |
| STAPHYLOCOCCUS AUREUS | $2.7 \times 10^6$ | $<2.0 \times 10^2$ | $<2.0 \times 10^2$ | $<2.0 \times 10^2$ |
| ENTEROCOCCUS FAECALIS | $1.2 \times 10^6$ | $2.2 \times 10^5$ | $8.0 \times 10^2$ | $<2.0 \times 10^2$ |
| CANDIDA ALBICANS | $2.4 \times 10^6$ | $<2.0 \times 10^2$ | $<2.0 \times 10^2$ | $<2.0 \times 10^2$ |
| ASPERGILLUS NIGER | $1.8 \times 10^6$ | $3.0 \times 10^5$ | $<2.0 \times 10^2$ | $<2.0 \times 10^2$ |

EXAMPLE 3

| Microorganisms | Inoculum micro-organisms/gram | Ageing at room temperature | | |
|---|---|---|---|---|
| | | 2 J | 7 J | 14 J |
| ESCHERICHIA COLI | $2.9 \times 10^6$ | $<2.0 \times 10^2$ | $<2.0 \times 10^2$ | $<2.0 \times 10^2$ |
| PSEUDOMONAS AERUGINOSA | $1.1 \times 10^6$ | $<2.0 \times 10^2$ | $<2.0 \times 10^2$ | $<2.0 \times 10^2$ |
| STAPHYLOCOCCUS AUREUS | $1.5 \times 10^6$ | $<2.0 \times 10^2$ | $<2.0 \times 10^2$ | $<2.0 \times 10^2$ |
| ENTEROCOCCUS FAECALIS | $2.2 \times 10^6$ | $<2.0 \times 10^4$ | $<2.0 \times 10^2$ | $<2.0 \times 10^2$ |
| CANDIDA ALBICANS | $3.6 \times 10^6$ | $<2.0 \times 10^2$ | $<2.0 \times 10^2$ | $<2.0 \times 10^2$ |
| ASPERGILLUS NIGER | $2.8 \times 10^6$ | $6.8 \times 10^3$ | $<2.0 \times 10^2$ | $<2.0 \times 10^2$ |

EXAMPLE 4

| Microorganisms | Inoculum micro-organisms/gram | Ageing at room temperature | | |
|---|---|---|---|---|
| | | 2 J | 7 J | 14 J |
| ESCHERICHIA COLI | $5.6 \times 10^6$ | $<2.0 \times 10^2$ | $<2.0 \times 10^2$ | $<2.0 \times 10^2$ |
| PSEUDOMONAS AERUGINOSA | $3.8 \times 10^6$ | $<2.0 \times 10^2$ | $<2.0 \times 10^2$ | $<2.0 \times 10^2$ |
| STAPHYLOCOCCUS AUREUS | $1.6 \times 10^6$ | $<2.0 \times 10^2$ | $<2.0 \times 10^2$ | $<2.0 \times 10^2$ |
| ENTEROCOCCUS FAECALIS | $2.8 \times 10^6$ | $7.5 \times 10^3$ | $<2.0 \times 10^2$ | $<2.0 \times 10^2$ |
| CANDIDA ALBICANS | $2.4 \times 10^6$ | $<2.0 \times 10^2$ | $<2.0 \times 10^2$ | $<2.0 \times 10^2$ |
| ASPERGILLUS NIGER | $1.6 \times 10^6$ | $1.2 \times 10^4$ | $<2.0 \times 10^2$ | $<2.0 \times 10^2$ |

COMPARATIVE EXAMPLES 5 to 11

Formulations of the same composition as that of Example 1 were tested, but replacing the antimicrobial protection system of the invention with conventional preserving systems as indicated below.

| Formulation | Sodium methyl p-hydroxy-benzoate | Ethyl alcohol | Germal 115* | Chlor-hexidine digluconate | Chloro-butanol | Chlor-phenesine | Hydroxy-methyl glycinate | Anti-microbial protection |
|---|---|---|---|---|---|---|---|---|
| Ex. 5 | 0.4% | 5% | — | — | — | — | — | insufficient |
| Ex. 6 | — | — | 0.3% | — | — | 0.3% | — | insufficient |
| Ex. 7 | 0.4% | — | 0.3% | — | — | — | — | insufficient |
| Ex. 8 | 0.4% | — | — | 0.25% | — | — | — | insufficient |
| Ex. 9 | 0.4% | — | — | 1% | — | — | — | insufficient |
| Ex. 10 | 0.4% | — | — | — | 0.5% | — | — | insufficient |
| Ex. 11 | 0.4% | — | — | — | — | — | 1% | insufficient |

*Germal 115: imidazolidinyl urea.

The antimicrobial protection of the formulations was evaluated by the artificial contamination test of "Challenge-test", as in the above examples, on the same microorganisms.

The results are judged insufficient.
They are indicated below.

EXAMPLE 5

| Microorganisms | Inoculum microorganisms/gram | Ageing at room temperature | | |
|---|---|---|---|---|
| | | 2 J | 7 J | 14 J |
| ESCHERICHIA COLI | $3.6 \times 10^6$ | $1.0 \times 10^4$ | $<2.0 \times 10^2$ | $<2.0 \times 10^2$ |
| PSEUDOMONAS AERUGINOSA | $2.0 \times 10^6$ | $<2.0 \times 10^2$ | $<2.0 \times 10^2$ | $<2.0 \times 10^2$ |
| STAPHYLOCOCCUS AUREUS | $1.4 \times 10^6$ | $1.2 \times 10^6$ | $9.2 \times 10^3$ | $<2.0 \times 10^2$ |
| ENTEROCOCCUS FAECALIS | $2.4 \times 10^6$ | $2.9 \times 10^6$ | $3.2 \times 10^6$ | $1.0 \times 10^6$ |
| CANDIDA ALBICANS | $1.9 \times 10^6$ | $3.6 \times 10^3$ | $<2.0 \times 10^2$ | $<2.0 \times 10^2$ |
| ASPERGILLUS NIGER | $1.2 \times 10^6$ | $1.0 \times 10^6$ | $<2.0 \times 10^2$ | $<2.0 \times 10^2$ |

EXAMPLE 6

| Microorganisms | Inoculum microorganisms/gram | Ageing at room temperature | | |
|---|---|---|---|---|
| | | 2 J | 7 J | 14 J |
| ESCHERICHIA COLI | $4.0 \times 10^6$ | $<2.0 \times 10^2$ | $<2.0 \times 10^2$ | $<2.0 \times 10^2$ |
| PSEUDOMONAS AERUGINOSA | $5.2 \times 10^6$ | $<2.0 \times 10^2$ | $<2.0 \times 10^2$ | $<2.0 \times 10^2$ |
| STAPHYLOCOCCUS AUREUS | $1.5 \times 10^6$ | $3.6 \times 10^5$ | $6.0 \times 10^2$ | $<2.0 \times 10^2$ |
| ENTEROCOCCUS FAECALIS | $2.2 \times 10^6$ | $2.6 \times 10^6$ | $4.2 \times 10^5$ | $1.8 \times 10^4$ |
| CANDIDA ALBICANS | $3.6 \times 10^6$ | $9.4 \times 10^4$ | $4.0 \times 10^2$ | $<2.0 \times 10^2$ |
| ASPERGILLUS NIGER | $2.2 \times 10^6$ | $2.0 \times 10^6$ | $1.8 \times 10^6$ | $4.5 \times 10^4$ |

EXAMPLE 7

| Microorganisms | Inoculum microorganisms/gram | Ageing at room temperature | | |
|---|---|---|---|---|
| | | 2 J | 7 J | 14 J |
| ESCHERICHIA COLI | $4.0 \times 10^6$ | $4.6 \times 10^4$ | $<2.0 \times 10^2$ | $<2.0 \times 10^2$ |
| PSEUDOMONAS AERUGINOSA | $5.2 \times 10^6$ | $<2.0 \times 10^2$ | $<2.0 \times 10^2$ | $<2.0 \times 10^2$ |
| STAPHYLOCOCCUS AUREUS | $1.5 \times 10^6$ | $8.6 \times 10^9$ | $3.6 \times 10^4$ | $<2.0 \times 10^2$ |
| ENTEROCOCCUS FAECALIS | $2.2 \times 10^6$ | $2.8 \times 10^6$ | $2.8 \times 10^6$ | $8.4 \times 10^9$ |
| CANDIDA ALBICANS | $3.6 \times 10^6$ | $1.4 \times 10^6$ | $<2.0 \times 10^2$ | $<2.0 \times 10^2$ |
| ASPERGILLUS NIGER | $2.2 \times 10^6$ | $1.6 \times 10^6$ | $<2.0 \times 10^2$ | $<2.0 \times 10^2$ |

EXAMPLE 8

| Microorganisms | Inoculum microorganisms/gram | Ageing at room temperature | | |
|---|---|---|---|---|
| | | 2 J | 7 J | 14 J |
| ESCHERICHIA COLI | $4.0 \times 10^6$ | $8.0 \times 10^5$ | $1.4 \times 10^4$ | $<2.0 \times 10^2$ |
| PSEUDOMONAS AERUGINOSA | $5.2 \times 10^6$ | $4.0 \times 10^2$ | $<2.0 \times 10^2$ | $<2.0 \times 10^2$ |
| STAPHYLOCOCCUS AUREUS | $1.5 \times 10^6$ | $7.0 \times 10^5$ | $6.5 \times 10^5$ | $1.2 \times 10^5$ |
| ENTEROCOCCUS FAECALIS | $2.2 \times 10^4$ | $3.1 \times 10^6$ | $4.0 \times 10^6$ | $3.2 \times 10^6$ |
| CANDIDA ALBICANS | $3.6 \times 10^6$ | $7.8 \times 10^4$ | $<2.0 \times 10^2$ | $<2.0 \times 10^2$ |
| ASPERGILLUS NIGER | $2.2 \times 10^6$ | $8.8 \times 10^5$ | $<2.0 \times 10^2$ | $<2.0 \times 10^2$ |

EXAMPLE 9

| Microorganisms | Inoculum microorganisms/gram | Ageing at room temperature | | |
|---|---|---|---|---|
| | | 2 J | 7 J | 14 J |
| ESCHERICHIA COLI | $2.5 \times 10^6$ | $1.8 \times 10^5$ | $<2.0 \times 10^2$ | $<2.0 \times 10^2$ |
| PSEUDOMONAS AERUGINOSA | $1.4 \times 10^6$ | $1.8 \times 10^6$ | $<2.0 \times 10^2$ | $<2.0 \times 10^2$ |
| STAPHYLOCOCCUS AUREUS | $2.1 \times 10^6$ | $1.6 \times 10^6$ | $1.3 \times 10^6$ | $2.1 \times 10^4$ |
| ENTEROCOCCUS FAECALIS | $4.3 \times 10^6$ | $2.0 \times 10^7$ | $3.3 \times 10^6$ | $2.0 \times 10^6$ |
| CANDIDA ALBICANS | $1.1 \times 10^6$ | $6.0 \times 10^2$ | $<2.0 \times 10^2$ | $<2.0 \times 10^2$ |
| ASPERGILLUS NIGER | $1.6 \times 10^7$ | $1.6 \times 10^5$ | $<2.0 \times 10^2$ | $<2.0 \times 10^2$ |

EXAMPLE 10

| Microorganisms | Inoculum microorganisms/gram | Ageing at room temperature | | |
|---|---|---|---|---|
| | | 2 J | 7 J | 14 J |
| ESCHERICHIA COLI | $4.2 \times 10^6$ | $1.8 \times 10^6$ | $<2.0 \times 10^2$ | $<2.0 \times 10^2$ |
| PSEUDOMONAS AERUGINOSA | $1.9 \times 10^6$ | $<2.0 \times 10^2$ | $<2.0 \times 10^2$ | $<2.0 \times 10^2$ |
| STAPHYLOCOCCUS AUREUS | $1.6 \times 10^6$ | $1.8 \times 10^6$ | $1.2 \times 10^6$ | $5.4 \times 10^4$ |
| ENTEROCOCCUS FAECALIS | $2.0 \times 10^6$ | $2.3 \times 10^6$ | $2.0 \times 10^6$ | $2.0 \times 10^6$ |
| CANDIDA ALBICANS | $1.4 \times 10^6$ | $8.0 \times 10^4$ | $<2.0 \times 10^2$ | $<2.0 \times 10^2$ |
| ASPERGILLUS NIGER | $1.0 \times 10^6$ | $2.8 \times 10^6$ | $4.0 \times 10^3$ | $<2.0 \times 10^2$ |

EXAMPLE 11

| Microorganisms | Inoculum microorganisms/gram | Ageing at room temperature | | |
|---|---|---|---|---|
| | | 2 J | 7 J | 14 J |
| ESCHERICHIA COLI | $2.5 \times 10^6$ | $<2.0 \times 10^2$ | $<2.0 \times 10^2$ | $<2.0 \times 10^2$ |
| PSEUDOMONAS AERUGINOSA | $1.4 \times 10^6$ | $<2.0 \times 10^2$ | $<2.0 \times 10^2$ | $<2.0 \times 10^2$ |
| STAPHYLOCOCCUS AUREUS | $2.1 \times 10^6$ | $5.0 \times 10^5$ | $<2.0 \times 10^2$ | $<2.0 \times 10^2$ |
| ENTEROCOCCUS FAECALIS | $4.3 \times 10^6$ | $2.5 \times 10^6$ | $2.5 \times 10^6$ | $1.6 \times 10^5$ |
| CANDIDA ALBICANS | $1.1 \times 10^6$ | $<2.0 \times 10^2$ | $<2.0 \times 10^2$ | $<2.0 \times 10^2$ |
| ASPERGILLUS NIGER | $1.6 \times 10^7$ | $<2.0 \times 10^2$ | $<2.0 \times 10^2$ | $<2.0 \times 10^2$ |

The tests of antimicrobial efficacy carried out on the formulations containing standard preserving systems showed that the antimicrobial protection imparted by these preserving systems was insufficient, even when chlorohexidine digluconate was used, which is known to be an excellent preserving agent.

EXAMPLE 12

A fluid lipstick of the composition below is prepared:

| | |
|---|---|
| brown iron oxide | 4 g |
| 1,2-pentanediol | 3 g |
| ethyl alcohol | 5 g |
| sodium methyl p-hydroxybenzoate | 0.4 g |
| Aqueous dispersion of polyurethane containing 49% solids, sold under the name "Sancure 2255" by the company Sancor | 100 g qs |

The procedure is the same as in Example 1.

EXAMPLE 13

A semi-permanent body make-up, optionally containing a sufficient amount of fragrance, is prepared in accordance with Example 1.

EXAMPLE 14

A fluid lipstick identical to that of Example 1 is prepared, except that the acrylic copolymer "Neocryl A-1090" is replaced with "Neocryl A-523" which is an acrylic copolymer in aqueous emulsion containing 60% solids, sold by the company Zeneca.

What is claimed is:

1. A method of plasticizing film-forming polymer particles and preventing microbial growth in a cosmetic or dermatological composition which can be applied to any one of the skin, keratin fibres, semi-mucous membranes and mucous membranes, comprising combining a cosmetic or dermatological composition comprising an aqueous dispersion of film-forming polymer particles with an antimicrobial protection system comprising 1,2-pentanediol.

2. A method of making up, protecting and/or non-therapeutically treating any one of the skin, keratin fibres, semi-mucous membranes and mucous membranes, comprising applying a cosmetic or dermatological composition comprising an aqueous dispersion of film-forming polymer particles combined with an antimicrobial protection system comprising 1,2-pentanediol, to said skin, keratin fibres, semi-mucous membranes or mucous membranes.

3. A method of obtaining a glossy film on skin, keratin fibres, semi-mucous membranes or mucous membranes which is at least one of non-sticky after drying, transfer-resistant and long-lasting comprising applying a cosmetic or dermatological composition comprising a film-forming polymer particles and 1,2-pentanediol to said skin, keratin fibres, semi-mucous membranes or mucous membranes.

4. The method of claim 1 wherein said composition is in the form of a lipstick, a foundation, a blusher, an eyeshadow, a mascara, an eyeliner, a nail varnish, a care composition, an antisun composition, a dermatological or pharmaceutical composition to be applied to the skin, semi-mucous membranes, or mucous membranes, or a self-tanning composition.

5. The method of claim 1 wherein said composition in the form of a lipstick, a lip care composition or a body make-up composition.

6. The method of claim 1 wherein said film-forming polymer is selected from the group consisting of anionic polyurethanes, cationic polyurethanes, nonionic polyurethanes, amphoteric polyurethanes, acrylic polyurethanes, polyurethane-polyvinylpyrrolidones, polyester-polyurethanes, polyether-polyurethanes, polyureas, polyurea-polyurethanes, polyesters, polyesteramides, fatty-chain polyesters, polyamides, epoxy ester resins, acrylic polymers and copolymers, vinyl polymers and copolymers, acrylic/vinyl copolymers, acrylic/silicone copolymers, nitrocellulose/acrylic copolymers, polymers of natural origin, modified polymers of natural origin, polymers resulting from the radical polymerization of one or more radical monomers, inside and/or partially at the surface of pre-existing particles of at least one polymer selected from the group consisting of polyurethanes polyureas, polyesters, polyesteramides and alkyds, and mixtures thereof.

7. The method of claim 6, in which the film-forming polymer is selected from the group consisting of acrylic polymers and copolymers, vinyl polymers and copolymers and acrylic/vinyl copolymers.

8. The method of claim 6, in which the film-forming polymer is a copolymer selected from the group consisting of (meth)acrylic acid/(meth)acrylate, (meth)acrylic acid/α-methylstyrene, (meth)acrylate/styrene, (meth)acrylic acid/styrene, (meth)acrylate/(meth)acrylate and (meth)acrylate/α-methylstyrene copolymers.

9. The method of claim 6 wherein the film-forming polymer is a copolymer derived from the copolymerization $C_1$–$C_8$ alkyl methacrylate monomers, optionally combined with one of acrylic acid, styrene and α-methylstyrene.

10. The method of claim 1 wherein the size of the polymer particles in aqueous dispersion is between 5 and 500 nm.

11. The method of claim 1 wherein the antimicrobial protection system comprises 0.1 to 10% by weight of 1,2-pentanediol, and at least one of 0 to 5% by weight of sodium methyl p-hydroxybenzoate and 0 to 40% by weight of ethyl alcohol.

12. The method of claim 11 wherein the antimicrobial protection system comprises 1 to 1% by weight of 1,2-pentanediol, and at least one of 0.05 to 2% by weight of sodium methyl p-hydroxybenzoate and 0.5 to 30% by weight of ethyl alcohol.

13. The method of claim 12 wherein the antimicrobial protection system comprises 3 to 5% by weight of 1,2-pentanediol, and at least one of 0.2 to 1% by weight of sodium methyl p-hydroxybenzoate and 1 to 10% by weight of ethyl alcohol.

14. A cosmetic or dermatological composition which can be applied to any one of the skin, keratin fibres, semi-mucous membranes and mucous membranes, comprising an aqueous dispersion of film-forming polymer particles combined with an antimicrobial protection system comprising 1,2-pentanediol.

15. The composition according to claim 14, which is in the form of a make-up composition, a care composition, an antisun or self-tanning composition or a dermatological or pharmaceutical composition, to be applied to the skin, keratin fibres, semi-mucous membranes or mucous membranes.

16. The composition according to claim 14 which is in the form of a lipstick, a foundation, a blusher, an eyeshadow, an eyeliner, a mascara, a nail varnish or a make-up product for the body.

17. A make-up composition for the lips or the body which comprises the composition of claim 14.

18. The composition according to claim 14 wherein the film-forming polymer is selected from the group consisting of anionic polyurethanes, cationic polyurethanes, nonionic polyurethanes, amphoteric polyurethanes, acrylic polyurethanes, polyurethane-polyvinylpyrrolidones, polyester-polyurethanes, polyether-polyurethanes, polyureas, polyurea-polyurethanes, polyesters, polyesteramides, fatty-chain polyesters, polyamides, epoxy ester resins, acrylic polymers and copolymers, vinyl polymers and copolymers, acrylic/vinyl copolymers, acrylic/silicone polymers, nitrocellulose/acrylic copolymers, polymers of natural origin, which are optionally modified, polymers resulting from the radical polymerization of one or more radical monomers, inside and/or partially at the surface of pre-existing particles of at least one polymer selected from the group consisting of polyurethanes, polyureas, polyesters, polyesteramides and alkyds, and mixtures thereof.

19. The composition according to claim 18, wherein the film-forming polymer is selected from vinyl polymers and copolymers, acrylic polymers and copolymers and vinyl/acrylic copolymers.

20. The composition according to claim 19, wherein the film-forming polymer is a copolymer selected from the group consisting of copolymers of (meth)acrylic acid/(meth)acrylate, (meth)acrylic acid/α-methyl-styrene, (meth)acrylate/styrene, (meth)acrylic acid/styrene, (meth)acrylate/(meth)acrylate and (meth)acrylate/ α-methylstyrene.

21. The composition according to claim 19, wherein the film-forming polymer is a copolymer derived from the copolymerization of $C_1$–$C_8$ alkyl methacrylate monomers, optionally combined with one of acrylic acid, styrene and α-methylstyrene.

22. The composition according to claim 14 wherein the size of the polymer particles in aqueous dispersion is between 5 and 500 nm.

23. The composition according to claim 14 wherein the antimicrobial protection system comprises 0.1 to 10% by weight of 1,2-pentanediol, and at least one of 0 to 5% by weight of sodium methyl p-hydroxybenzoate and 0 to 40% by weight of ethyl alcohol.

24. The composition according to claim 23, wherein the antimicrobial protection system comprises 1 to 7% by weight of 1,2-pentanediol, and at least one of 0.05 to 2% by weight of sodium methyl p-hydroxybenzoate and 0.5 to 30% by weight ethyl alcohol.

25. The composition according to claim 24, wherein the antimicrobial protection system comprises 3 to 5% by weight of 1,2-pentanediol, and at least one of 0.2 to 1% by weight of sodium methyl p-hydroxybenzoate and 1 to 10% by weight of ethyl alcohol.

26. The composition according to claim 14, further comprising at least one of a water-soluble dye, a pigment, a filler and a pearlescent agent.

27. The composition according to claim 14, further comprising at least one additive selected from the group consisting of thickeners, dispersing agents, antifoaming agents, oils, waxes and cosmetics or dermatological active agents.

28. A process for the antimicrobial protection of a composition containing an aqueous dispersion of film-forming polymer particles, the process consisting of introducing into the composition an antimicrobial protection system comprising 1,2-pentanediol.

29. A cosmetic or dermatological composition which can be applied to any one of the skin, keratin fibres, semi-mucous membranes and mucous membranes, consisting essentially of an aqueous dispersion of film-forming polymer particles combined with an antimicrobial protection system comprising 1,2-pentanediol.

30. The composition according to claim 29, which is in the form of a make-up composition, a care composition, an antisun or self-tanning composition or a dermatological or pharmaceutical composition, to be applied to the skin, keratin fibres, semi-mucous membranes or mucous membranes.

31. The composition according to claim 29 which is in the form of a lipstick, a foundation, a blusher, an eyeshadow, an eyeliner, a mascara, a nail varnish or a make-up product for the body.

32. A make-up composition for the lips or the body which comprises the composition of claim 29.

33. The composition according to claim 29 wherein the film-forming polymer is selected from the group consisting of anionic polyurethanes, cationic polyurethanes, nonionic polyurethanes, amphoteric polyurethanes, acrylic polyurethanes, polyurethane-polyvinylpyrrolidones, polyester-polyurethanes, polyether-polyurethanes, polyureas, polyurea-polyurethanes, polyesters, polyesteramides, fatty-chain polyesters, polyamides, epoxy ester resins, acrylic polymers and copolymers, vinyl polymers and copolymers, acrylic/vinyl copolymers, acrylic/silicone copolymers, nitrocellulose/acrylic copolymers, polymers of natural origin, which are optionally modified, polymers resulting from the radical polymerization of one or more radical monomers, inside and/or partially at the surface of pre-existing particles of at least one polymer selected from the group consisting of polyurethanes, polyureas, polyesters, polyesteramides and alkyds, and mixtures thereof.

34. The composition according to claim 33, wherein the film-forming polymer is selected from vinyl polymers and copolymers, acrylic polymers and copolymers and vinyl/acrylic copolymers.

35. The composition according to claim 34, wherein the film-forming polymer is a copolymer selected from the group consisting of copolymers of (meth)acrylic acid/(meth) acrylate, (meth)acrylic acid/α-methyl-styrene, (meth) acrylate/styrene, (meth)acrylic acid/styrene, (meth)acrylate/(meth)acrylate and (meth)-acrylate/α-methylstyrene.

36. The composition according to claim 34, wherein the film-forming polymer is a copolymer derived from the copolymerization of $C_1$–$C_8$ alkyl methacrylate monomers, optionally combined with one of acrylic acid, styrene and α-methylstyrene.

37. The composition according to claim 29 wherein the size of the polymer particles in aqueous dispersion is between 5 and 500 nm.

38. The composition according to claim 29, further comprising at least one of a water-soluble dye, a pigment, a filler and a pearlescent agent.

39. The composition according to claim 29, further comprising at least one additive selected from the group consisting of thickeners, dispersing agents, antifoaming gents, oils, waxes and cosmetic or dermatological active agents.

40. The composition according to claim 23, which is in the form of a make-up composition, a care composition, an antisun or self-tanning composition or a dermatological or pharmaceutical composition, to be applied to the skin, keratin fibres, semi-mucous membranes or mucous membranes.

41. The composition according to claim 23 which is in the form of a lipstick, a foundation, a blusher, an eyeshadow, an eyeliner, a mascara, a nail varnish or a make-up product for the body.

42. A make-up composition for the lips or the body which comprises the composition of claim 23.

43. The composition according to claim 23 wherein the film-forming polymer is selected from the group consisting of anionic polyurethanes, cationic polyurethanes, nonionic polyurethanes, amphoteric polyurethanes, acrylic polyurethanes polyurethane-polyvinylpyrrolidones, polyester-polyurethanes, polyether-polyurethanes, polyureas, polyurea-polyurethanes, polyesters, polyesteramides, fatty-chain polyesters, polyamides, epoxy ester resins, acrylic polymers and copolymers, vinyl polymers and copolymers, acrylic/vinyl copolymers, acrylic/silicone copolymers, nitrocellulose/acrylic copolymers, polymers of natural origin, which are optionally modified, polymers resulting from the radical polymerization of one or more radical monomers, inside and/or partially at the surface of pre-existing particles of at least one polymer selected from the group consisting of polyurethanes, polyureas, polyesters, polyesteramides and alkyds, and mixtures thereof.

44. The composition according to claim 43, wherein the film-forming polymer is selected from vinyl polymers and copolymers, acrylic polymers and copolymers and vinyl/acrylic copolymers.

45. The composition according to claim 43, wherein the film-forming polymer is a copolymer selected from the group consisting of copolymers of (meth)acrylic acid/(meth) acrylate, (meth)acrylic acid/α-methyl-styrene, (meth) acrylate/styrene, (meth)acrylic acid/styrene, (meth)acrylate/(meth)acrylate and (meth)-acrylate/α-methylstyrene.

46. The composition according to claim 43, wherein the film-forming polymer is copolymer derived from the copolymerization of $C_1$–$C_8$ alkyl methacrylate monomers, optionally combined with one of acrylic acid, styrene and α-methylstyrene.

47. The composition according to claim 23 wherein the size of the polymer particles in aqueous dispersion is between 5 and 500 nm.

48. The composition according to claim 23, further comprising at least one of a water-soluble dye, a pigment, a filler and a pearlescent agent.

49. The composition according to claim 23, further comprising at least one additive selected from the group consisting of thickeners, dispersing agents, antifoaming agents, oilx, waxes and cosmetic or dermatological active agents.

* * * * *